United States Patent
Tanaka

(10) Patent No.: US 8,454,497 B2
(45) Date of Patent: Jun. 4, 2013

(54) ENDOSCOPE APPARATUS AND BENDING DRIVE CONTROL METHOD

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 160 days.

(21) Appl. No.: 13/026,784

(22) Filed: Feb. 14, 2011

(65) Prior Publication Data

US 2011/0275896 A1 Nov. 10, 2011

Related U.S. Application Data

(63) Continuation of application No. PCT/JP2010/061590, filed on Jul. 8, 2010.

(30) Foreign Application Priority Data

Sep. 30, 2009 (JP) .................................. 2009-228025

(51) Int. Cl.
*A61B 1/005* (2006.01)

(52) U.S. Cl.
USPC ............................. 600/146; 600/145; 600/118

(58) Field of Classification Search
USPC ................................... 600/117, 118, 145, 146
See application file for complete search history.

(56) References Cited

U.S. PATENT DOCUMENTS

| | | | | |
|---|---|---|---|---|
| 5,469,840 A * | 11/1995 | Tanii et al. | ..................... | 600/117 |
| 6,511,417 B1 * | 1/2003 | Taniguchi et al. | ............ | 600/117 |
| 6,551,237 B2 * | 4/2003 | Matsui | ......................... | 600/118 |
| 8,147,402 B2 * | 4/2012 | Tanaka et al. | ................. | 600/117 |
| 8,211,009 B2 * | 7/2012 | Tanaka et al. | ................. | 600/117 |
| 2007/0027361 A1 | 2/2007 | Uchimura et al. | | |
| 2007/0173694 A1 | 7/2007 | Tsuji et al. | | |
| 2009/0048488 A1 * | 2/2009 | Uchimura | ..................... | 600/152 |
| 2009/0149711 A1 | 6/2009 | Tanaka et al. | | |
| 2010/0204547 A1 * | 8/2010 | Tanaka et al. | ................. | 600/145 |

FOREIGN PATENT DOCUMENTS

| | | |
|---|---|---|
| EP | 1 800 593 A1 | 6/2007 |
| EP | 2 070 465 A1 | 6/2009 |
| JP | 08-000542 | 1/1996 |
| JP | 2005-287969 | 10/2005 |
| JP | 2006-116289 | 5/2006 |
| JP | 2007-151862 | 6/2007 |
| JP | 2009-136618 | 6/2009 |
| WO | WO 2005/094664 A1 | 10/2005 |
| WO | WO 2006/035693 A1 | 4/2006 |

* cited by examiner

*Primary Examiner* — John P Leubecker
(74) *Attorney, Agent, or Firm* — Scully, Scott, Murphy & Presser, P.C.

(57) ABSTRACT

An endoscope apparatus includes: an insertion portion including a bending portion provided on a distal end side thereof; a bending drive section that drives bending of the bending portion; an insertion shape detection section that detects an insertion shape of the distal end side of the insertion portion as insertion shape information; a curved state detection section that detects a curved state based on the insertion shape information as curve information; a plane calculation section that performs a calculation to estimate a plane for driving bending of the bending portion from the detected curve information; and a bending control section that drives bending of the bending drive section along the estimated plane.

14 Claims, 14 Drawing Sheets

FIG.17
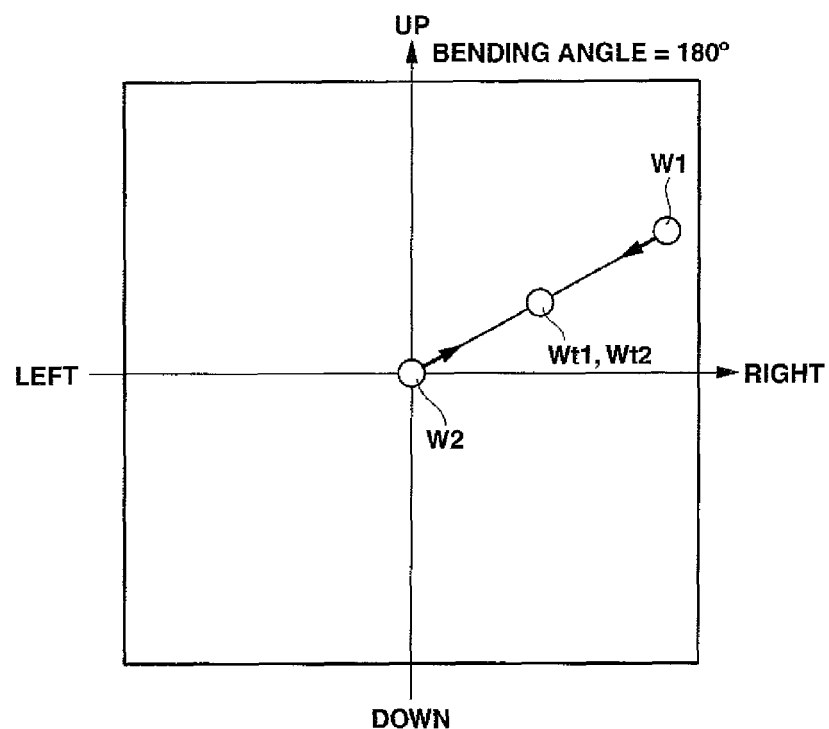
FIG.18
(A) 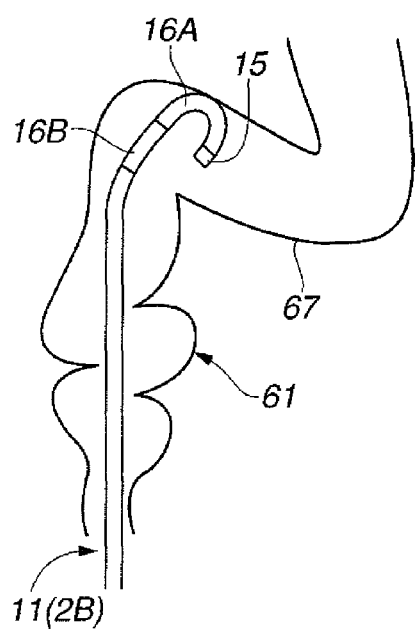
(B) 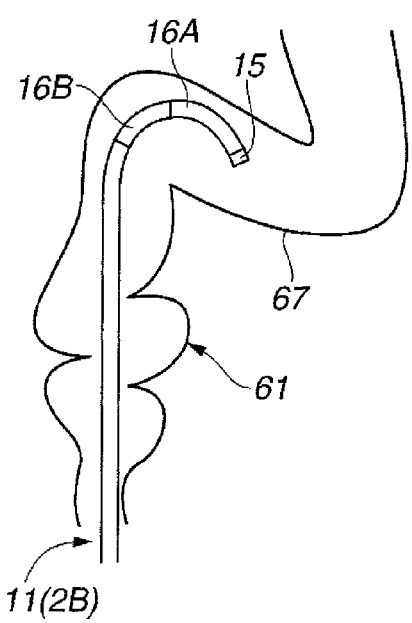

ENDOSCOPE APPARATUS AND BENDING DRIVE CONTROL METHOD

CROSS REFERENCE TO RELATED APPLICATION

This application is a continuation application of PCT/JP2010/061590 filed on Jul. 8, 2010 and claims benefit of Japanese Application No. 2009-228025 filed in Japan on Sep. 30, 2009, the entire contents of which are incorporated herein by this reference.

BACKGROUND OF THE INVENTION

1. Field of the Invention

The present invention relates to an endoscope apparatus that electrically drives bending of a bending portion of an endoscope, and a bending drive control method.

2. Description of the Related Art

Endoscopes with image pickup means and a bendable bending portion on a distal end side of an insertion portion are widely used for inspection, examination or the like of an inside of a body cavity.

Also, smooth insertion of an insertion portion into an intricately-curved body cavity such as a large intestine may require skills. For example, a transverse colon in a large intestine sags and causes difficulty in insertion of an insertion portion to a hepatic flexure side on a deep part side as it is. Therefore, in general, what is called "flip-up" is performed as an insertion procedure for removing a sag of a transverse colon to straighten the transverse colon.

For example, Japanese Patent Application Laid-Open Publication No. 2006-116289 discloses an endoscope apparatus that uses information on an insertion (curve) shape of a distal end side of an insertion portion, which is calculated based on detection of positions of position detection coils arranged in a longitudinal direction of the insertion portion, in addition to an image picked up by image pickup means provided at a distal end portion of the insertion portion, in order to facilitate smooth insertion of the insertion portion.

SUMMARY OF THE INVENTION

An endoscope apparatus according to the present invention includes:
an insertion portion including a bendable bending portion provided on a distal end side thereof;
a bending drive section that drives bending of the bending portion;
an insertion shape detection section that detects an insertion shape of the insertion portion as insertion shape information;
a curved state detection section that detects a curved state of the insertion portion based on the insertion shape information, as curve information,
a plane calculation section that performs a calculation to estimate a plane for driving bending of the bending portion from the curve information detected by the curved state detection section; and
a bending control section that drives bending of the bending drive section along the plane.

A bending drive control method according to the present invention includes:
a curve plane estimation step of estimating a curve plane including a distal end side of an insertion portion, the insertion portion including a bendable bending portion provided thereon, when the distal end side of the insertion portion is inserted along a curved curve shape in a tubular body cavity;
a virtual plane setting step of setting a virtual plane in the vicinity of a distal end of the insertion portion, with an axis direction of the distal end side of the insertion portion as a normal direction thereof; and
a bending drive direction determination step of determining a bending drive direction to drive bending of the bending portion, based on an intersection line between the curve plane and the virtual plane.

BRIEF DESCRIPTION OF THE DRAWINGS

FIG. 17 is a diagram illustrating a case where bending of first and second bending portions is driven.

FIG. 18 is a diagram illustrating a case where a distal end side of an insertion portion is inserted into a large intestine in the fourth embodiment.

DETAILED DESCRIPTION OF THE PREFERRED EMBODIMENT(S)

Hereinafter, embodiments of the present invention will be described with reference to the drawings.

First Embodiment

Figure 1:
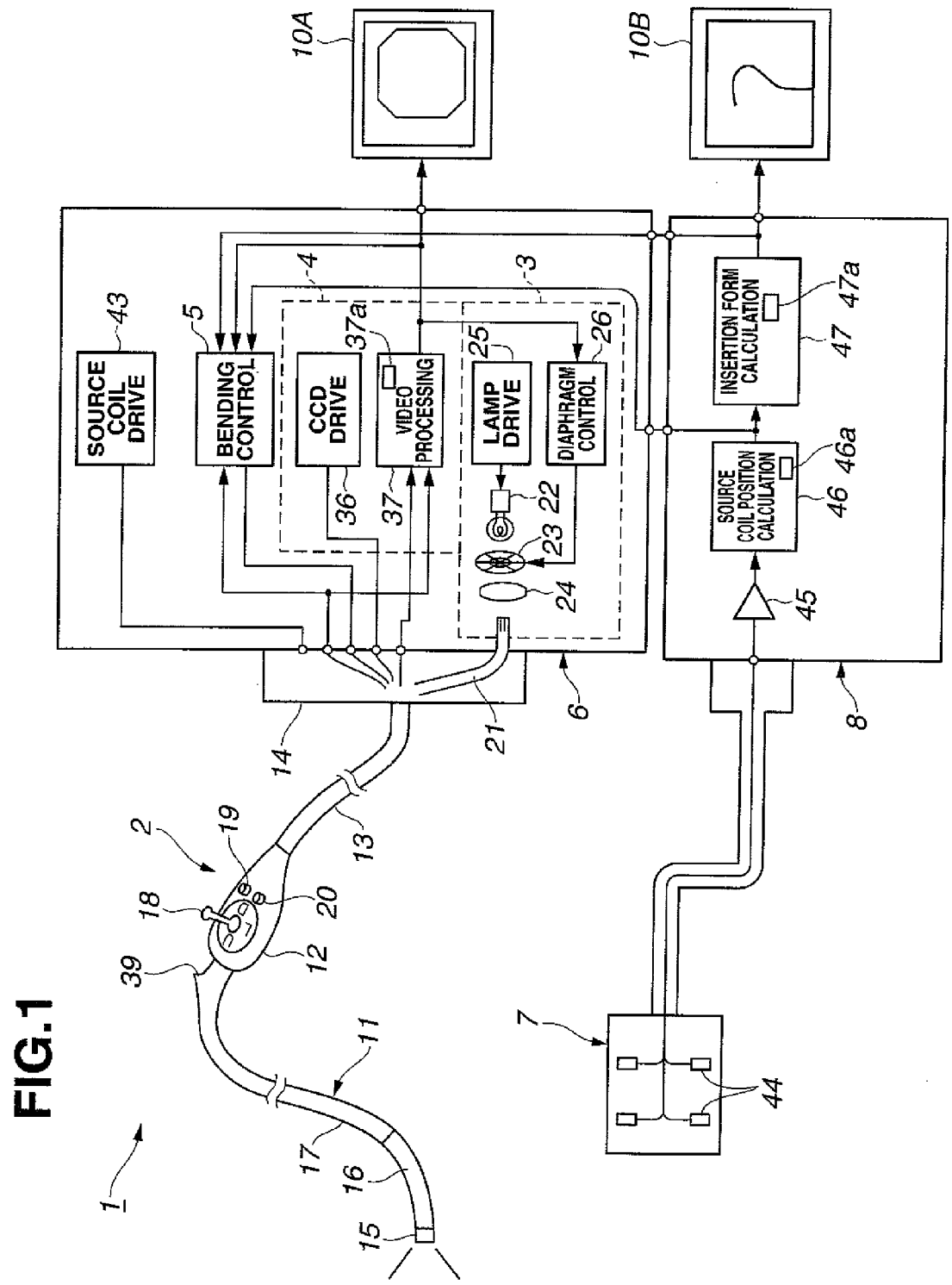
FIG. 1 is a diagram illustrating an overall configuration of an endoscope apparatus according to a first embodiment of the present invention.

As illustrated in FIG. 1, an endoscope apparatus 1 according to a first embodiment of the present invention includes an endoscope 2 to be inserted into, e.g., a body cavity, a light source section 3 that supplies illuminating light to the endoscope 2, a signal processing section 4 that performs signal processing for image pickup means included in the endoscope 2, and a video processor 6 including, e.g., a bending control section 5 that performs control of bending of an bending portion of the endoscope 2, therein.

The endoscope apparatus 1 further includes: a sensing coil unit 7 that detects positions of source coils for position detection provided in the endoscope 2; an insertion shape detection apparatus 8 that detects an insertion shape of an insertion portion 11 of the endoscope 2 by means of a detection signal from the sensing coil unit 7 and creates an image thereof; and monitors 10A and 10B that display an endoscope image picked up by the image pickup means and an insertion shape detection image created by the insertion shape detection apparatus 8, respectively.

The endoscope 2 includes the elongated insertion portion 11 to be inserted into a body cavity, an operation section 12 provided at a rear end of the insertion portion 11, and a universal cord 13 extending from the operation section 12. A connector 14 at a rear end of the universal cord 13 is detachably connected to the video processor 6.

Also, the insertion portion 11 includes: a rigid distal end portion 15 provided at a distal end thereof; a bending portion 16 bendably provided adjacent to a rear end of the distal end portion 15; and a flexible tube portion 17, which has a long length and flexibility, extending from a rear end of the bending portion 16 up to a front end of the operation section 12.

The operation section 12 is provided with a bending joystick 18 as bending instruction operation means for performing an operation to provide an instruction for a bending direction and a bending angle of the bending portion 16, a mode selection switch 19 for selection between an automatic bending (automatic insertion) mode and a manual bending (manual insertion) mode, and a scope switch 20 that, e.g., gives an instruction to display a still image.

Where the automatic bending mode is selected, the bending control section 5 automatically determines a bending drive direction of the bending portion 16, and a surgeon simply performs work for pushing the insertion portion 11 into a deep part side. Where the manual bending mode is selected, the surgeon operates the joystick 18 to provide an instruction for a bending drive direction of the bending portion 16, and the bending drive section 5 determines the bending drive direction according to the instruction as a bending drive direction for the bending portion 16. Then, the surgeon performs work for pushing the insertion portion 11 into the deep part side.

A light guide 21 that conveys illuminating light is inserted through, e.g., the inside of the insertion portion 11 of the endoscope 2, and a rear end of the light guide 21 projects from the connector 14, forming an incident end face.

Illuminating light provided by a lamp 22 included in the light source section 3 is made to enter the incident end face via a diaphragm 23 and a condensing lens 24. The lamp 22 is lighted by lamp drive power supplied from a lamp drive circuit 25 and generates illuminating light.

The amount of the opening (the amount of the aperture) of the diaphragm 23 allowing the illuminating light to pass through is controlled by a diaphragm control circuit 26.

The illuminating light conveyed by the light guide 21 exits to the outside from a light guide distal end face fixed to the distal end portion 15 of the insertion portion 11 further through an illumination lens 27 (see FIG. 2) attached to an illuminating window, and illuminates an object such as a diseased part in a body cavity.

Figure 2:
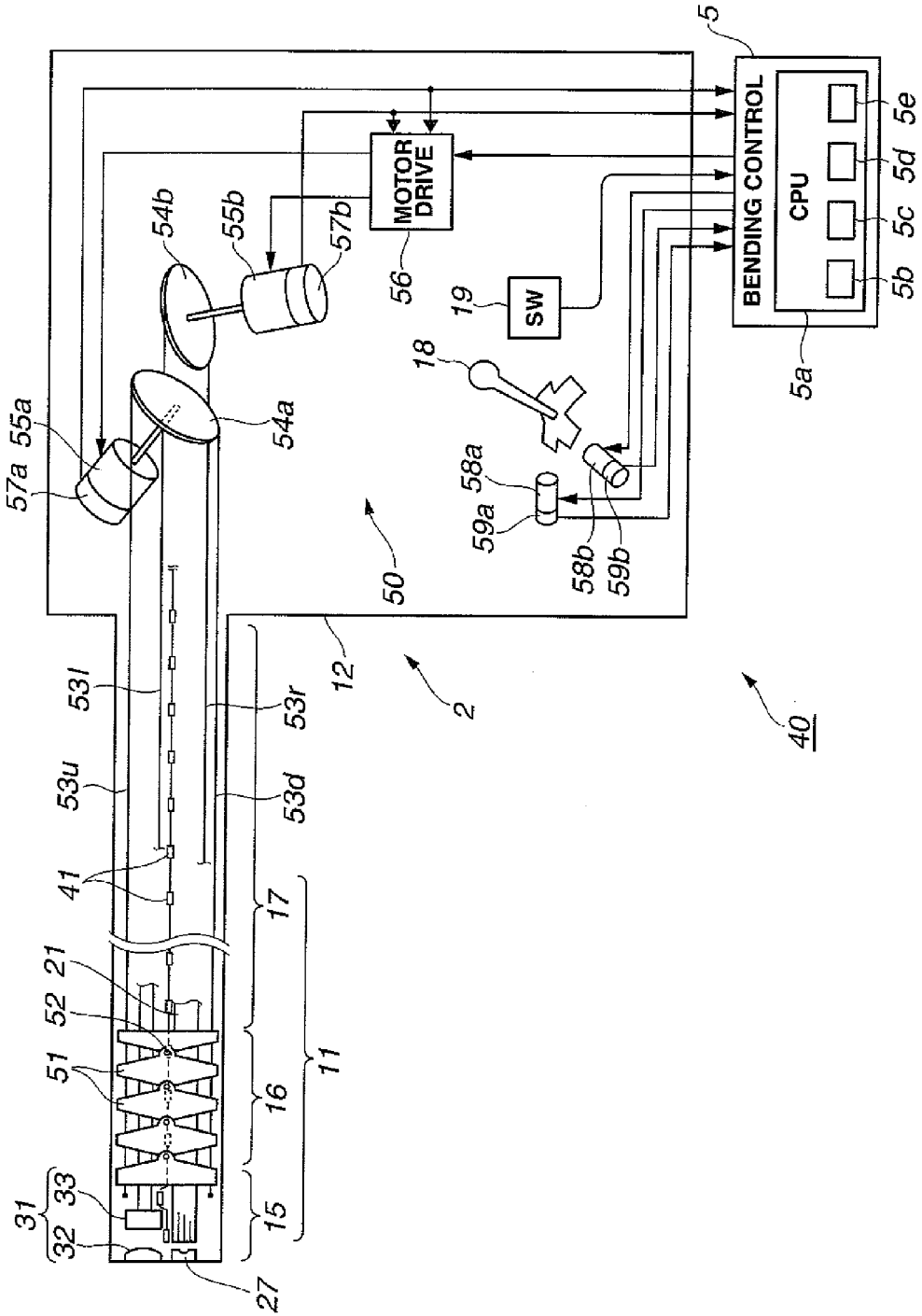
FIG. 2 is a diagram illustrating configurations of an endoscope and a bending control apparatus.

As illustrated in FIG. 2, the distal end portion 15 is provided with an observation window (adjacent to the illuminating window), and an image pickup unit 31 is attached to the observation window.

The image pickup unit 31, which is attached to a non-illustrated lens frame, includes an objective lens 32 that forms an optical image of the object, and a charge-coupled device (abbreviated as "CCD") 33 as an image pickup device with an image pickup surface thereof arranged at a position where an image is formed by the objective lens 32.

A cable connected to the CCD 33 is inserted through, e.g., the insertion portion 11, and as illustrated in FIG. 1, a rear end side thereof is connected to a CCD drive circuit 36 and a video processing circuit 37, which are included in the signal processing section 4, via an electrical connection point in the connector 14.

The CCD drive circuit 36 generates a CCD drive signal and applies the CCD drive signal to the CCD 33. As a result of the application of the CCD drive signal, the CCD 33 performs photoelectric conversion of the optical image formed on the image pickup surface and outputs the image in the form of a CCD output signal.

The CCD output signal is inputted to the video processing circuit 37, and the video processing circuit 37 creates a video signal for displaying the optical image on the image pickup surface of the CCD 33 as an endoscope image, and outputs the video signal to the monitor 10A, whereby the endoscope image is displayed on a display screen of the monitor 10A.

The CCD 33 is arranged so as to have a predetermined relationship with a bending direction of the bending portion 16 in the insertion portion 11. More specifically, an upward direction of the image pickup surface of the CCD 33 is an upward direction of the bending portion 16 from among upward/downward and leftward/rightward bending directions.

The video signal is inputted to the diaphragm control circuit 26, and the diaphragm control circuit 26 calculates an average brightness by, e.g., integrating a luminance signal component of the video signal in a predetermined cycle. The opening amount of the diaphragm 23 is adjusted using a signal of a difference resulting from subtracting a reference value corresponding to a proper brightness from the average brightness signal as a diagraph control signal. Then, automatic light control is performed so that the amount of illuminating light passing through the diaphragm 23 has the reference value.

The video processing circuit 37 includes a dark part detection circuit 37a that detects whether or not a dark part exists in the endoscope image by means of image processing. Information on the detection (determination) of whether or not a dark part exists by the dark part detection circuit 37a is sent to the bending control section 5.

When the automatic bending mode in which the insertion portion 11 is automatically bent is selected, normally, the bending control section 5 controls the bending drive direction and the bending amount (bending angle) of the bending portion 16 so that the distal end portion 15 is headed for (is directed to) the dark part, with the dark part as a target position for insertion.

On the other hand, in the manual insertion mode, a surgeon operates the joystick 18 to set the bending drive direction and the bending amount (bending angle) of the bending portion 16 so that the distal end portion 15 is headed for the dark part, with the dark part as a target position for insertion.

A non-illustrated treatment instrument channel is provided in the insertion portion 11, and a rear end side of the treatment instrument channel communicates with a treatment instrument insertion opening 39 provided in the vicinity of the front end of the operation section 12.

Also, the bending portion 16 is provided adjacent to the rear end of the distal end portion 15 of the insertion portion 11, and the bending control section 5 provided in the video processor 6 is configured to control a power-operated bending drive mechanism 50 such as illustrated in FIG. 2. The bending drive mechanism 50 and the bending control section 5 in FIG. 2 are included in a bending control apparatus 40.

Respective adjacent parts of a plurality of bending pieces 51 included in the bending portion 16 are pivotably connected in a longitudinal direction of the bending portion 16 via rivets 52.

Bending directions of the respective bending pieces 51 are determined depending on the positions where the rivets 52 are provided, and the rivets 52 are arranged alternately or at arbitrary intervals at left-right positions and up-down positions, enabling the bending portion 16 to be bent in an arbitrary direction in addition to the leftward/rightward directions and the upward/downward directions.

In FIG. 2, only the rivets 52 for upward/downward bending are illustrated for simplicity. Angle wires (bending wires) 53u and 53d, and 53l and 53r, which can be bent upward/downward and leftward/rightward are inserted through the insertion portion 11, and distal ends of the angle wires 53u and 53d, and 53l and 53r are secured to the distal end portion 15.

Rear ends of the angle wires 53u and 53d, and 53l and 53r are fixed to an upward/downward bending pulley 54a and a leftward/rightward bending pulley 54b in the operation section 12.

The pulleys 54a and 54b are freely subjected to normal/reverse rotation by means of electric motors 55a and 55b included in bending drive means for electrically driving bending of the bending portion 16. The electric motors 55a and 55b are driven by motor drive signals from a motor drive section 56. The motor drive section 56 is controlled by the bending control section 5.

Although FIG. 1 illustrates an example configuration in which the bending control section 5 is provided inside the video processor 6, the bending control section 5 may be provided inside the endoscope 2 such as the inside of the operation section 12.

The electric motors 55a and 55b driven by motor drive signals from the motor drive section 56 rotate the pulleys 54a and 54b, and as a result of the rotation of the pulleys 54a and 54b, the angle wires 53u, 53d, 53l and 53r are pulled, thereby driving bending of the bending portion 16.

When the pulleys 54a and 54b are rotated, the amounts of pulling of the angle wires 53u, 53d, 53l and 53r are determined so as to correspond to rotational angles of the pulleys 54a and 54b, and the bending portion 16 is bent according to the pulling amounts. Accordingly, detection of the rotational angles of the electric motors 55a and 55b or the pulleys 54a and 54b, or the pulling amount (movement amount) of the angle wires 53u, 53d, 53l and 53r enables detection of the bending angle of the bending portion 16.

The present embodiment provides a configuration in which the bending angle of the bending portion 16 is detected via the rotational angles of the pulleys 54a and 54b by means of, for example, rotary encoders (hereinafter abbreviated as "encoders") 57a and 57b attached to shaft portions of the electric motors 55a and 55b.

That is to say, the rotational angles of the pulleys 54a and 54b, in other words, the bending angle of the bending portion 16 corresponding to the rotational angles of the pulleys 54a and 54b, can be detected based on output signals from the encoders 57a and 57b. Accordingly, the encoders 57a and 57b are included in bent shape detection means for detecting a bent shape of the bending portion 16.

Pulley angle or bending angle detection signals (detection values) based on the output signals from the encoders 57a and 57b are inputted to the motor drive section 56. Instructed values for the bending drive direction and the bending angle provided via the joystick 18 as the bending instruction operation means are inputted to the motor drive section 56 via the bending control section 5.

Then, the motor drive section 56 drives the electric motors 55a and 55b to rotate so that the values detected by the encoders 57a and 57b follow (correspond to) the instructed values.

The bending control section 5 provides the instructed values provided by the bending instruction operation means, to the motor drive section 56, and the motor drive section 56 drives the electric motors 55a and 55b to rotate to bend the bending portion 16 to an instructed predetermined bending angle so that the detection value of the bending angle becomes the instructed value.

As a result of a surgeon performing an operation to tilt the joystick 18 provided in the operation section 12 in an arbitrary bending direction in the upward/downward and leftward/rightward directions, the direction in which the joystick 18 is tilted becomes an instructed value for the bending drive direction and the angle of the tilting becomes an instructed value for the bending angle.

As a result of the surgeon performing an instructive operation in which the joystick 18 is tilted in an arbitrary direction in the upward/downward and leftward/rightward directions, an upward/downward direction joystick motor 58a and a leftward/rightward direction joystick motor 58b rotate according to the direction of the tilting.

The rotational angles thereof are detected by encoders 59a and 59b, and the detection signals from the encoders 59a and 59b are inputted to the bending control section 5 as instructed values for the bending drive direction and the bending angle. The joystick motors 58a and 58b are controlled by the bending control section 5, and the detection signals from the encoders 59a and 59b are also inputted to the bending control section 5.

Then, the bending control section 5 outputs the instructed values for the bending drive direction and the bending angle as the detection signals from the encoders 59a and 59b, to the motor drive section 56 to control the operation thereof.

Also, source coils 41 are arranged, for example, at predetermined intervals in the insertion portion 11 along a longitudinal direction thereof, and as illustrated in FIG. 1, a signal line connected to the source coils 41 is connected to a source coil drive circuit 43 provided in the video processor 6 via an electrical connection point in the connector 14.

The source coil drive circuit 43 sequentially applies an alternating-current drive signal to the respective source coils 41 via the signal line to generate an alternating-current magnetic field around the respective source coils 41.

At a predetermined position such as a part around a bed on which a non-illustrated patient, to which the insertion portion 11 is to be inserted, is laying, as illustrated in FIG. 1, the sensing coil unit 7 including a plurality of sensing coils 44 is arranged, and the magnetic fields generated by the source coils 41 arranged in the insertion portion 11 are detected by means of the plurality of sensing coils 44.

Then, detection signals from the sensing coils 44 are amplified by an amplifier 45 in the insertion shape detection apparatus 8 and then inputted to a source coil position calculation circuit 46. The source coil position calculation circuit 46 calculates the positions of the respective source coils 41 from amplitude values and phase values of the signals detected by the sensing coils 44.

Information on the positions calculated by the source coil position calculation circuit 46 is inputted to an insertion shape calculation circuit 47. The insertion shape calculation circuit 47 detects an insertion shape (e.g., a curved curve shape) of the insertion portion 11 to be inserted into a body cavity from a shape formed by connecting the calculated positions of the respective source coils 41, and the detected insertion shape is modeled to create an insertion shape image signal.

In other words, the insertion shape calculation circuit 47 at least has a function of an insertion shape detection section 47a, which detects an insertion shape including the case of a curve shape on the distal end side of the insertion portion 11.

The insertion shape image signal created by the insertion shape calculation circuit 47 is inputted to the monitor 10B, and in a display screen thereof, an image of the insertion shape for, e.g., the case where the distal end side of the insertion portion 15 is curved, is displayed.

Also, information on coordinates of the insertion shape including the case of the curve shape on the distal end side of the insertion portion 11, which has been calculated by the insertion shape calculation circuit 47, is obtained by the bending control section 5. As described later, when the bending control section 5 performs control to drive bending of the bending portion 16, the bending control section 5 particularly uses information on coordinates of the curve (as information on coordinates of the insertion shape) in the state in which the distal end side of the insertion portion 11 is curved.

As illustrated in FIG. 2, the source coils 41 are attached also to the inside of the distal end portion 15, and the source coil position calculation circuit 46 calculates a specific direction in, e.g., the upward/downward and leftward/rightward directions in the circumferential direction of the distal end portion 15 in addition to the position of the distal end portion 15, from the positions of the plurality of source coils 41 attached to the distal end portion 15. In the distal end portion 15, the plurality of source coils 41 are arranged in a relationship in which the source coils 41 are arranged so as to deviate from a straight line to enable detection of the circumferential direction of the distal end portion 15.

The arrangement of the plurality of source coils 41 in the distal end portion 15 enables detection of a reference azimuth around an axis of the distal end portion 15, in addition to the position and the longitudinal direction (which is also referred to as "distal end portion direction") of the distal end portion 15.

In the distal end portion 15, the CCD 33 is arranged in a fixed manner, enabling detection of an upward direction of the image pickup surface thereof (corresponding to the twelve o'clock position in a clock, which is the direction from a lower position toward an upper position of a bending). In other words, the source coil position calculation circuit 46 has a function of a position and azimuth detection section 46a, which detects the position of the distal end portion 15 and a reference azimuth thereof. The position and azimuth detection section 46a has a function of azimuth detection means, which detects a reference azimuth of the bending portion 16.

Then, the source coil position calculation circuit 46 outputs information on the position and the reference azimuth of the distal end portion 15 to the bending control section 5.

The bending control section 5, which includes, for example, a CPU 5a, and the CPU 5a performs control to drive bending of the bending portion 16, using the inputted information on the position and the reference azimuth of the distal end portion 15.

Furthermore, the bending control section 5 in the present embodiment determines whether or not the position of the distal end portion 15 in the body cavity has reached a predetermined region. For the determination, the bending control section 5 detects a length of insertion from the insertion shape of the distal end portion 15 from the position where the distal end portion 15 is set at the position of an insertion opening of the body cavity to the position of the distal end portion 15 inserted into the body cavity.

For example, storing the positions of the source coils 41 arranged in the distal end portion 15 when the distal end portion 15 is set at the position of an anus enables detection of the length of insertion of the distal end portion 15 inserted into the large intestine.

Also, in the present embodiment, in order to smoothly insert the bending portion 16 to a deep part side of a transverse colon in a large intestine as a tubular body cavity, the bending control section 5 as bending control means estimates a plane (a later-described curve plane) suitable for flip-up to perform control to drive bending of the bending portion 16.

More specifically, the CPU 5a included in the bending control section 5 has a function of a curve plane estimation section 5b, which estimates (creates) a curve plane for a curve of the bending portion 16 or flexible tube portion 17 part of the insertion portion 11 inserted into a sagging transverse colon via a splenic flexure, as a curve plane. Also, the CPU 5a has a function of a virtual plane setting section 5c, which temporarily sets a virtual plane at the position of the distal end portion 15, the virtual plane having the direction of the distal end portion of the distal end portion 15 as a normal direction thereof, in order to determine a bending direction in which the bending portion 16 is to be bent along the curve plane (a plane parallel to the curve plane in the board sense).

Furthermore, as described later, the CPU 5a has a function of an angle calculation section 5d, which performs processing for calculating an intersection line between the curve plane and the virtual plane, and with a specific bending direction in the distal end portion 15 or the bending portion 16 as a reference azimuth, calculating the angle formed by the reference azimuth and the intersection line. The CPU 5a also has a function of a bending drive direction determination section 5e, which determines a direction along the intersection line to be a bending drive direction.

Next, an operation according to the present embodiment will be described with reference to the flowchart in FIG. 3.

When the endoscope apparatus 1 illustrated in FIG. 1 is powered on, the respective components of the endoscope apparatus 1 start operating. A surgeon inserts the distal end side of the insertion portion 11 of the endoscope 2 into a large intestine, which is an object to be examined in an endoscope examination, from an anus as indicated in step S1 in FIG. 3.

Upon start of insertion into the large intestine, the CPU 5a in the bending control section 5 obtains information on the insertion shape of the insertion portion 11 from the insertion shape detection apparatus 8 as indicated in step S2. Furthermore, in the next step S3, the CPU 5a obtains information on the coordinates of bending of the bending portion 16.

Also, in the next step S4, the CPU 5a obtains information on a dark part in an endoscope image from the dark part detection circuit 37a. Then, as indicated in step S5, the distal end side of the insertion portion 11 is inserted into a deep part side of the large intestine with the position of the dark part as the insertion target direction.

Also, as indicated in step S6, the CPU 5a monitors the length of the insertion to determine whether or not the distal end portion 15 has reached the inside of the transverse colon through the splenic flexure, as a predetermined region. In this case, the site of the splenic flexure in the large intestine is sharply curved, and thus, the CPU 5a may determine whether or not the predetermined region has been reached, by monitoring not only the length of the insertion but also information on the angle of the curve of the bending portion 16 to use information on whether or not there is a curve having an angle of no less than a predetermined angle.

If the CPU 5a has determined that the predetermined region has not been reached, the CPU 5a returns to the processing in step S2, and repeats the processing from steps S2 to S6.

On the other hand, if the distal end portion 15 has reached the inside of the transverse colon through the splenic flexure (in other words, the distal end side of the insertion portion 11 enters a state in which the distal end side is curved at the splenic flexure), the CPU 5a performs bending drive direction determination processing in step S7 and determines a bending drive target position in the determined bending drive direction in the next step S8, to perform control to drive bending of the bending portion 16. In other words, if the distal end side of the insertion portion 11 has reached the predetermined region, the CPU 5a performs control to drive bending of the bending portion 16, by a bending drive control method, which will be described later with reference to FIGS. 4 and 6.

In the next step S9, the distal end portion side is inserted into the deep part side of the transverse colon in a state in which bending of the bending portion 16 is driven to reach the bending drive target position.

Then, the distal end portion 15 is inserted through the hepatic flexure to reach a position in the vicinity of the ascending colon or the cecum, and then, the procedure for inserting the insertion portion 11 is terminated. Then, the surgeon conducts an endoscope examination while, for example, withdrawing the insertion portion 11.

Figure 4:
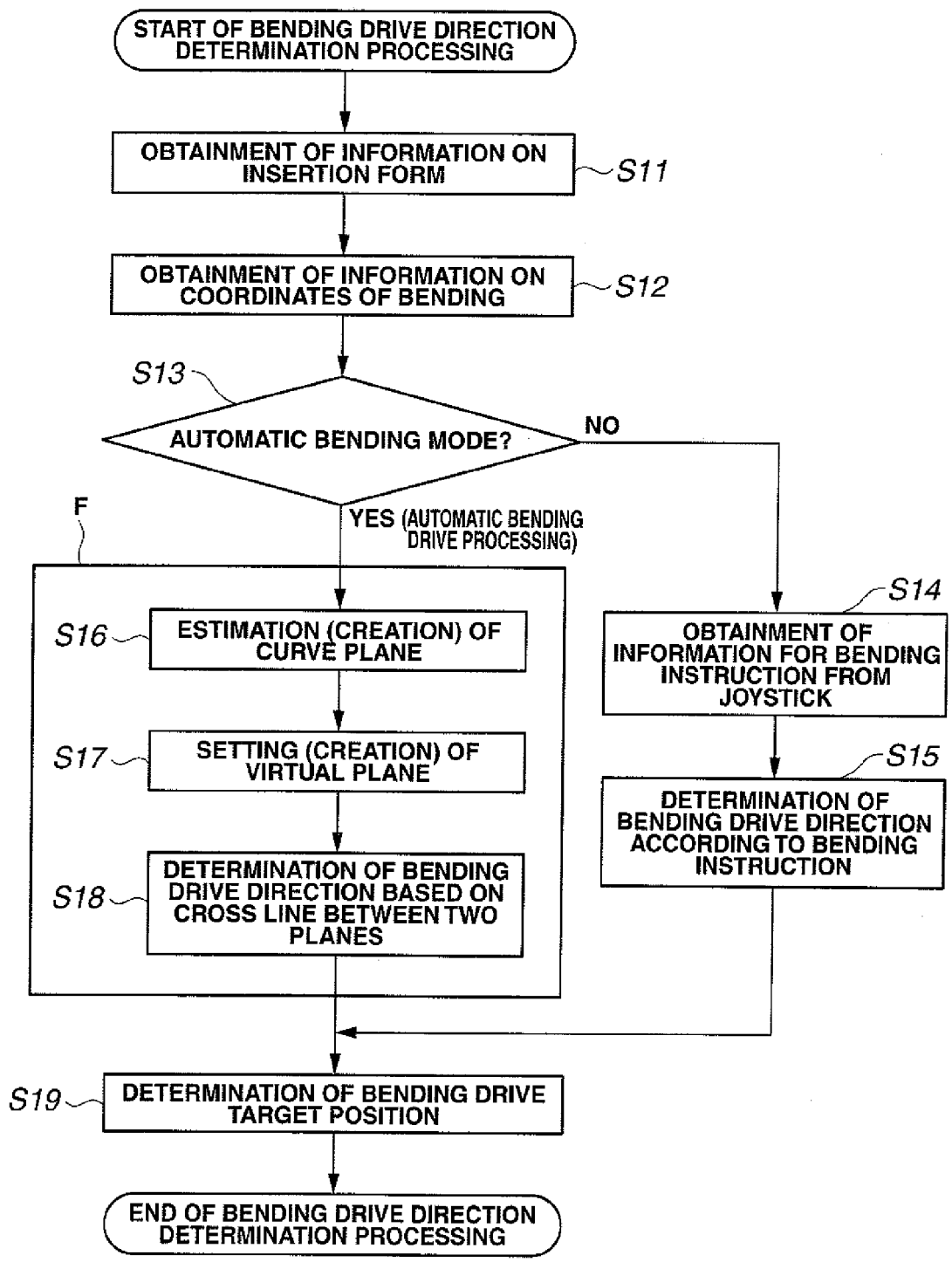
FIG. 4 is a flowchart illustrating a processing procedure for determining a bending drive direction for a predetermined region.

FIG. 4 illustrates a procedure for the bending drive direction determination processing in step S7. As can be understood from the description below, substantive bending drive direction determination processing lies in steps S16 to S18 surrounded by frame F in FIG. 4. Steps S16 to S18 provide a main processing procedure for a drive control method for driving bending of the bending portion 16.

When the bending drive direction determination processing is started, the CPU 5a obtains information on the insertion shape of the insertion portion 11 from the insertion shape detection apparatus 8, in the first step S11. In the next step S12, the CPU 5a obtains information on coordinates of a bending of the bending portion 16.

Figure 3:
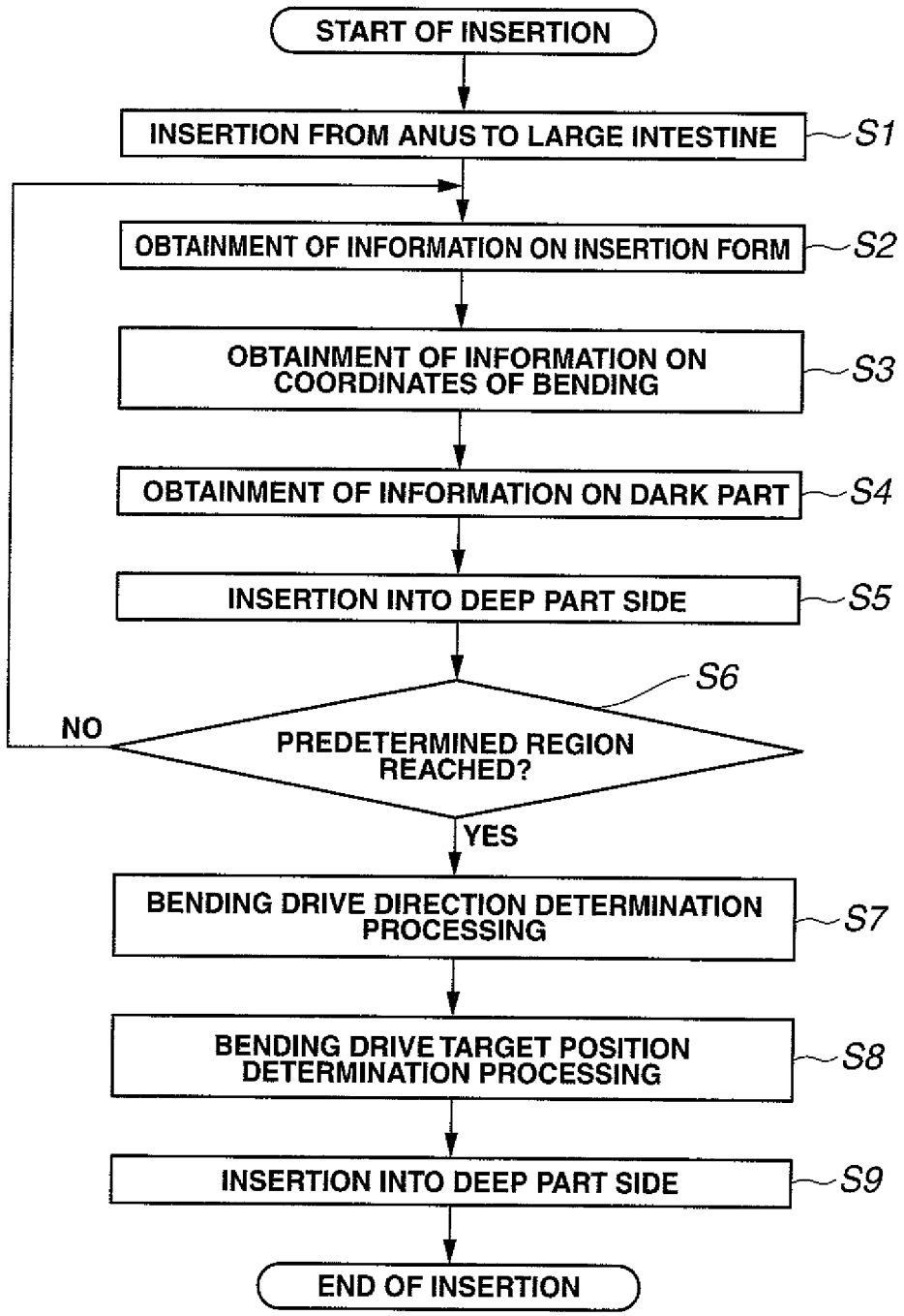
FIG. 3 is a flowchart illustrating a processing procedure for a case where an insertion portion is inserted into a large intestine.

Steps S11 and S12 provide processing that is the same as that in steps S2 and S3 in FIG. 3, and when the state of the distal end side of the insertion portion 11 has no change or only a small change, the information in steps S2 and S3 may be diverted.

In the next step S13, the CPU 5a determines whether or not the automatic bending mode has been set. If the automatic bending mode has not been set (in other words, the manual bending mode has been set), the CPU 5a obtains information corresponding to a bending instruction provided by the joystick 18 in response to the bending instruction via the encoders 59a and 59b in step S14.

In the next step S15, the CPU 5a determines a bending drive direction according to the bending instruction provided by the joystick 18, and advances to processing in step S19.

On the other hand, if the result of the determination in step S13 is that the automatic bending mode has been selected, the CPU 5a advances to processing in S16 providing the substantive bending drive direction determination processing as a mode of automatic bending drive processing, and in step S16, the CPU 5a performs processing for estimating (creating) a curve plane.

After the estimation of the curve plane as described later, in the next step S17, the CPU 5a performs processing for creating (setting) a virtual plane. Furthermore, in the next step S18, the CPU 5a performs processing for determining a bending drive direction based on an intersection line between the curve plane and the virtual plane, and advances to processing for determining a bending drive target position in the next step S19.

Figure 5:
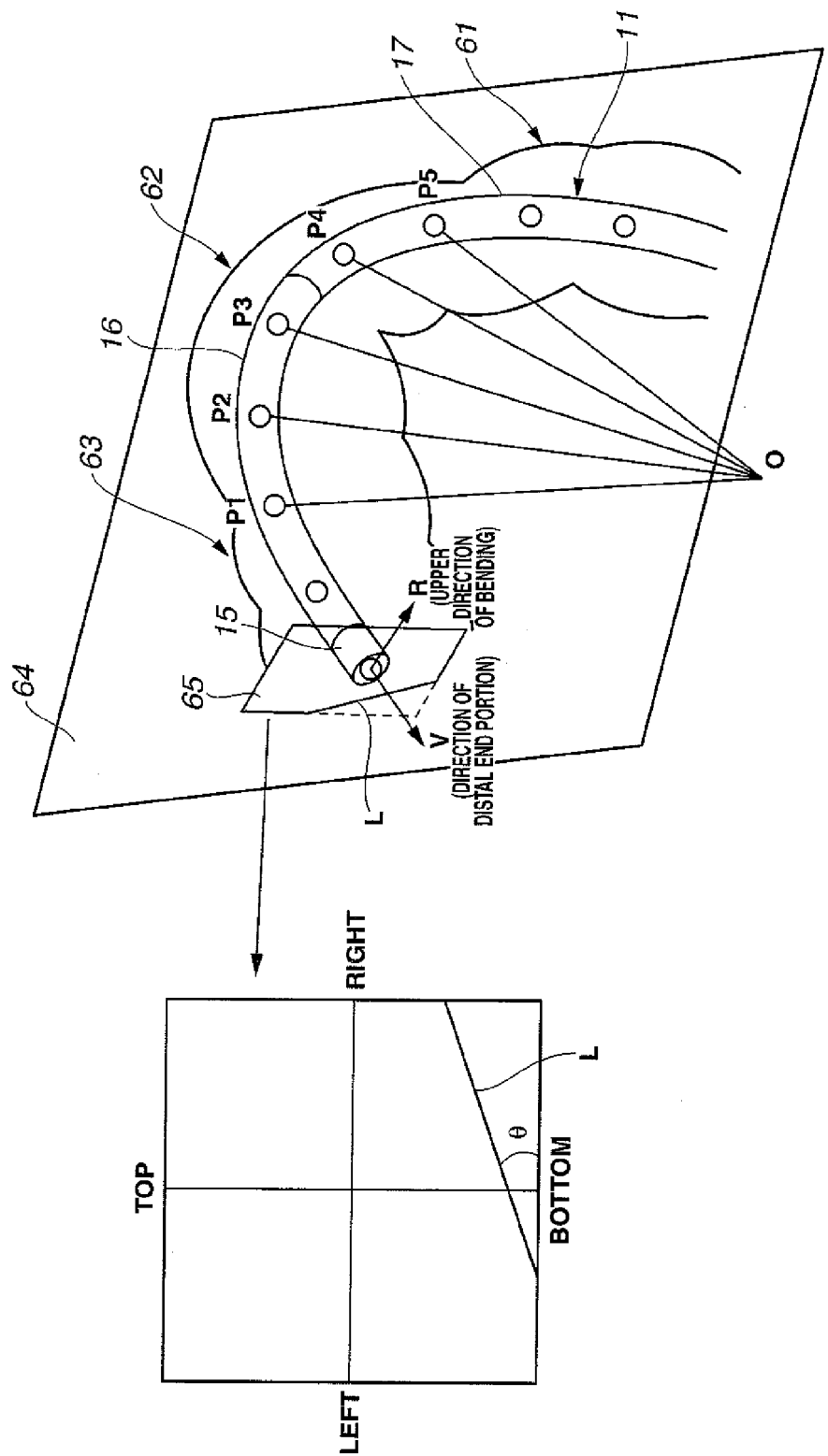
FIG. 5 is a diagram illustrating a state in which an insertion portion is inserted to reach a transverse colon side via a splenic flexure in a large intestine.
Figure 6:
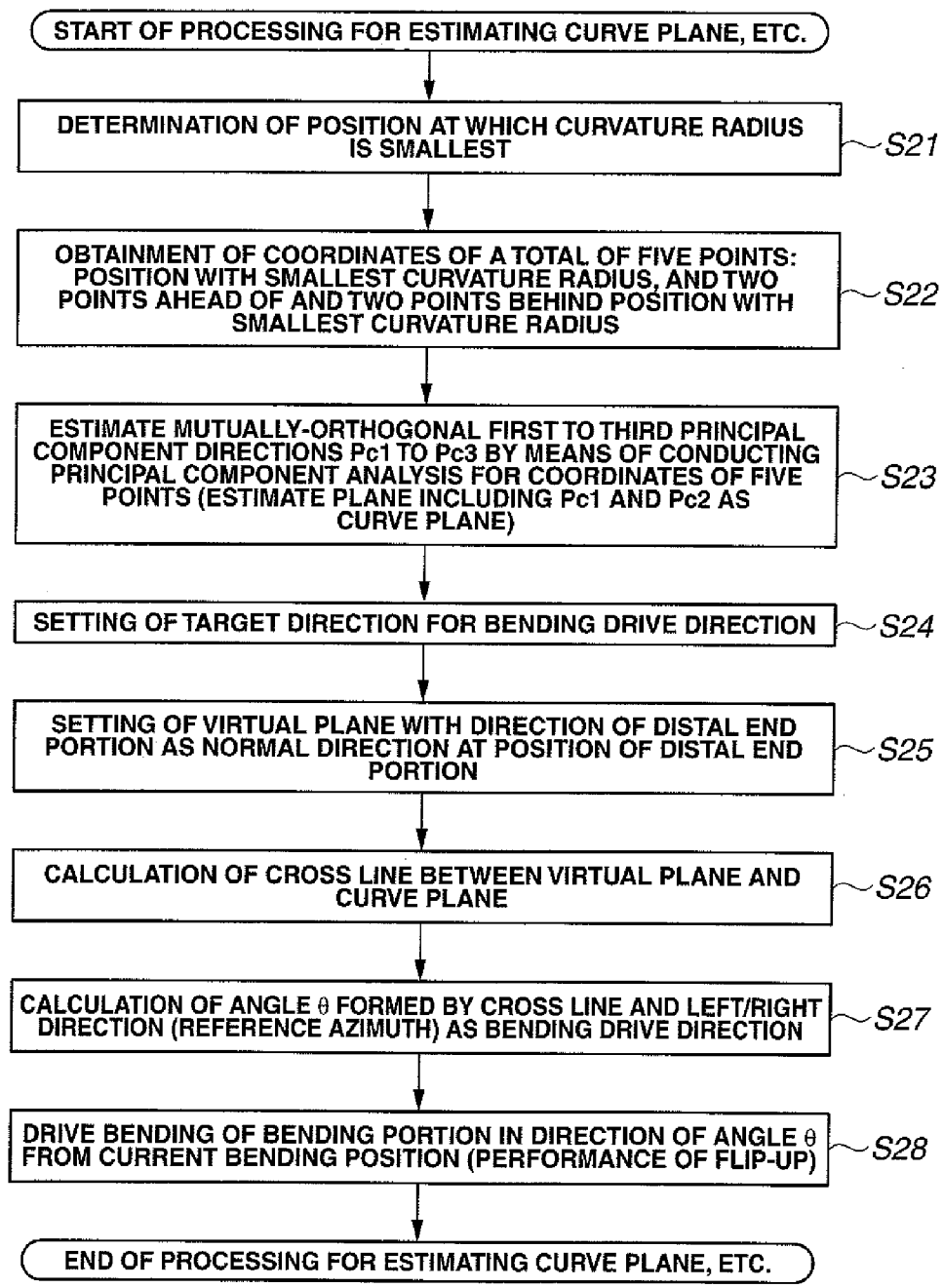
FIG. 6 is a flowchart illustrating a processing procedure for estimating a curve plane, etc., in the state in FIG. 5.

Next, a detailed processing procedure for estimating the curve plane, etc., in the above-described bending drive direction determination processing will be described with reference to FIGS. 5 and 6. FIG. 5 illustrates a state in which the distal end side of the insertion portion 11 of the endoscope 2 has been inserted up to a transverse colon 63 side via a splenic flexure 62 in a large intestine 61 as a predetermined region.

In a state in which the distal end side of the insertion portion 11 has been inserted into the predetermined region as described above, as indicated in step S21 in FIG. 6, the CPU 5a in the bending control section 5 determines a position P3 with a smallest curvature radius in position information for the insertion shape part (of the bending portion 16 or the flexible tube portion 17 on the distal end side of the insertion portion 11).

As illustrated in FIG. 5, the angle of a curve of the insertion portion 11 is the sharpest at the splenic flexure 62 part (which is sharply curved), and thus, determination of the position P3 with the smallest curvature radius enables determination of a reference position in the curved insertion portion 11 inside the splenic flexure 62.

In the next step S22, the CPU 5a obtains coordinates of two positions P1 and P2, and two positions P4 and P5, adjacent to the position P3 at proper intervals ahead of the positions P3 and behind the positions P3 (in other words, ahead of the positions P3 and behind the positions P3 in the longitudinal direction of the insertion portion 11), respectively, to obtain the coordinates of a total of the five points with the position P3 with the smallest curvature radius in the insertion shape part of the curved insertion portion 11 as the reference position. It should be noted that O in FIG. 5 indicates the origin of the coordinate system.

In this case, coordinates of the source coils 41 arranged at the predetermined intervals in the longitudinal direction of the insertion portion 11 may be used. It should be noted that the obtainment of the five points is one representative example and the number of points is not limited to this count.

In the next step S23, the CPU 5a conducts a principal component analysis (PCA) for the coordinates of the positions P1 to P5 of the obtained five points to estimate (derive) a first principal component direction Pc1, a second principal component direction Pc2, and a third principal component direction Pc3, which are mutually-orthogonal coordinate axes according to the coordinate distribution of the five points.

In this case, the first principal component direction Pc1 is a direction in which the coordinate data for the five points on the insertion portion 11 has the largest scattering (dispersion), and the second principal component direction Pc2, which is orthogonal to the first principal component direction Pc1, is a direction with the next largest dispersion. The third principal component direction Pc3 is a direction orthogonal to (a plane including) the first principal component direction Pc1 and the second principal component direction Pc2.

Figure 7A:
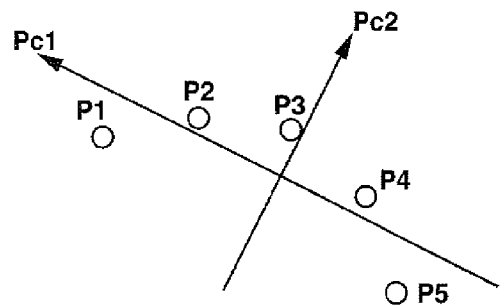
FIG. 7A is a diagram illustrating a first principal component direction and a second principal component direction, which are calculated for five points set on a curve plane according to a principal component analysis.

FIG. 7A illustrates the estimated first principal component direction Pc1 and the estimated second principal component directions Pc2. The plane including the first principal component direction Pc1 and the second principal component direction Pc2 is an estimated curve plane 64.

Figure 7B:
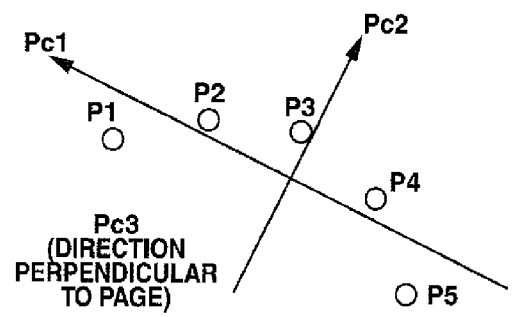
FIG. 7B is a diagram illustrating a third principal component direction perpendicular to a first principal component direction and a second principal component direction for five points set on a curve plane according to a principal component analysis.

FIG. 7B illustrates the estimated third principal component direction Pc3. The third principal component direction Pc3 is a normal direction perpendicular to the curve plane 64 for a curve in a state in which the distal end side part of the insertion portion 11 is curved at the splenic flexure 62. In other words, not only is the curve plane 64 estimated, but also a normal direction perpendicular to this is estimated, enabling estimation of a more accurate curve plane 64.

Accordingly, steps S21 to S23 provide curve plane estimation processing for estimating the curve plane 64.

In the next step S24, the CPU 5a checks a rotation direction of the curved insertion portion 11 as to whether the curved insertion portion 11 is rotated (curved) at the splenic flexure 62 in a clockwise direction (right-handed direction) or a counterclockwise direction (left-handed direction) (relative to an axis perpendicular to the curve plane 64), when the curve shape of the insertion portion 11 is traced from a proximal end side to the distal end side on the estimated curve plane 64. Then, the CPU 5a sets a direction opposite to the rotation direction as a target direction for the bending drive direction.

For the rotation direction or the opposite rotation direction in this case, the right-handed/the left-handed are distinguished by a sign of the exterior product of two vectors. More specifically, a sign of the exterior product of a first vector and a second vector set on the proximal end side and the distal end side, respectively, with the splenic flexure 62 interposed therebetween, along the insertion shape of the insertion portion 11 is set to the target direction for the bending drive direction. The target direction for the bending drive direction is set (estimated) by processing for obtaining the exterior product of the vectors.

Where the curved insertion shape in FIG. 5 has a left-handed rotation, the direction opposite to the rotation, that is, the right-handed rotation is the target direction for the bending drive direction.

In the next step S25, the CPU 5a performs the setting of a virtual plane in step S17 in FIG. 4. Therefore, the CPU 5a sets a virtual plane 65 with the distal end portion direction (vector V in FIG. 5) as a normal direction thereof, at the position of the distal end portion 15 (C0 in FIG. 5).

In this case, a reference azimuth such as an upward direction of the curve (which corresponds to the upward direction for the image pickup surface of the CCD 33, and a vector R in FIG. 5) is set as a reference direction for the virtual plane 65. In other words, a reference direction in the virtual plane 65 is associated with the reference azimuth so as to provide a correspondence or predetermined relationship therebetween.

In the next step S26, the CPU 5a calculates an intersection line L between the virtual plane 65 and the curve plane 64 (estimated by conducting a principal component analysis).

On the left side of FIG. 5, the intersection line L in the virtual plane 65 is illustrated in association with the up-down and left-right directions (of the bending portion 16 or the image pickup surface).

In the next step S27, the CPU 5a calculates (estimates) an angle $\theta$ formed by the intersection line L and the left-right direction as the bending drive direction.

In step S28 following the calculation of the bending drive direction as described above, the CPU 5a drives bending of the bending portion 16 in the direction of the angle $\theta$ from the current bending position, enabling with proper flip-up of the loose transverse colon 63 with good accuracy. Then, the processing in FIG. 6 is terminated.

Figure 8:
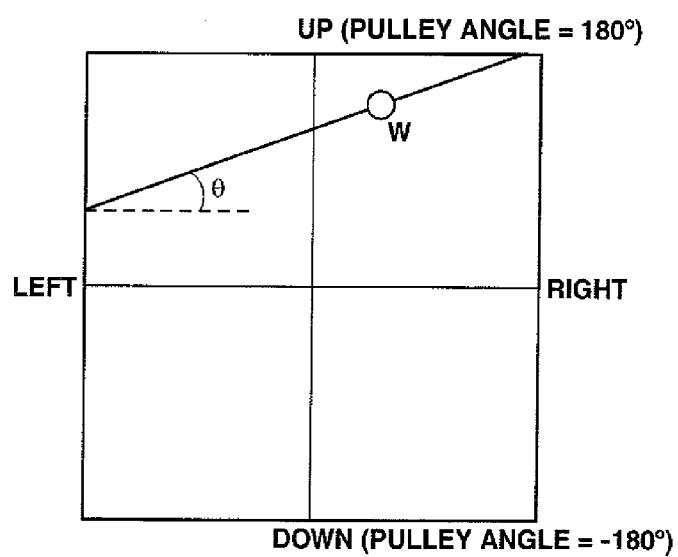
FIG. 8 is a diagram illustrating a direction in which bending of a bending portion from a current bending position is driven in a coordinate system for pulley angle.

FIG. 8 illustrates, e.g., a current bending position (bending drive position) W of the bending portion 16 in a coordinate system for pulley angle. The CPU 5a controls the driving of the electric motors 55a and 55b via the motor drive section 56, and the electric motors 55a and 55b drives bending of the bending portion 16 in the direction of the angle $\theta$ from the current bending position W, thereby performing flip-up by the distal end portion 15 side.

As a result of the loose transverse colon 63 being flipped up by the distal end portion 15 side, the transverse colon 63 can be set to be close to a straight line, enabling a surgeon to easily and smoothly insert the insertion portion 11.

According to the present embodiment providing the operation described above, using information on the curve shape of the distal end side of the insertion portion 11 inserted in a curved manner into the loose transverse colon 63 side through the splenic flexure 62, the curve plane 64 on which the bent shape lies can be estimated with good accuracy.

Then, bending of the bending portion 16 is driven in a direction opposite to the direction in which the bending portion 16 is curved on the curve plane 64, enabling highly-accurate flip-up for setting the transverse colon 63 to be in a state close to a straight line, facilitating smooth insertion of the insertion portion 11.

The present embodiment is not limited to the case where bending of the bending portion 16 is driven on the curve plane 64, and bending of the bending portion 16 may be driven along a plane parallel to the curve plane 64.

Also, the present embodiment is not limited to the case where a flip-up is performed when the distal end side of the insertion portion 11 is inserted into the transverse colon 63 side from the splenic flexure 62, and may be applied to cases where the distal end side of the insertion portion 11 is inserted into another site. Furthermore, e.g., the method for estimating the curve plane 64 in the present embodiment can widely be applied to cases where the insertion portion 11 is inserted into a curved tubular body cavity.

Second Embodiment

Next, a second embodiment of the present invention will be described. In the first embodiment, the insertion portion 11 of the endoscope 2 is provided with one bending portion 16 at the rear end of the distal end portion 15.

Meanwhile, an endoscope 2B according to the present embodiment is a two step-bending endoscope whose insertion portion 11 is provided with a first bending portion 16A, which corresponds to the bending portion 16 in the first embodiment, and a second bending portion 16B at a rear end of the first bending portion 16A.

Figure 9:
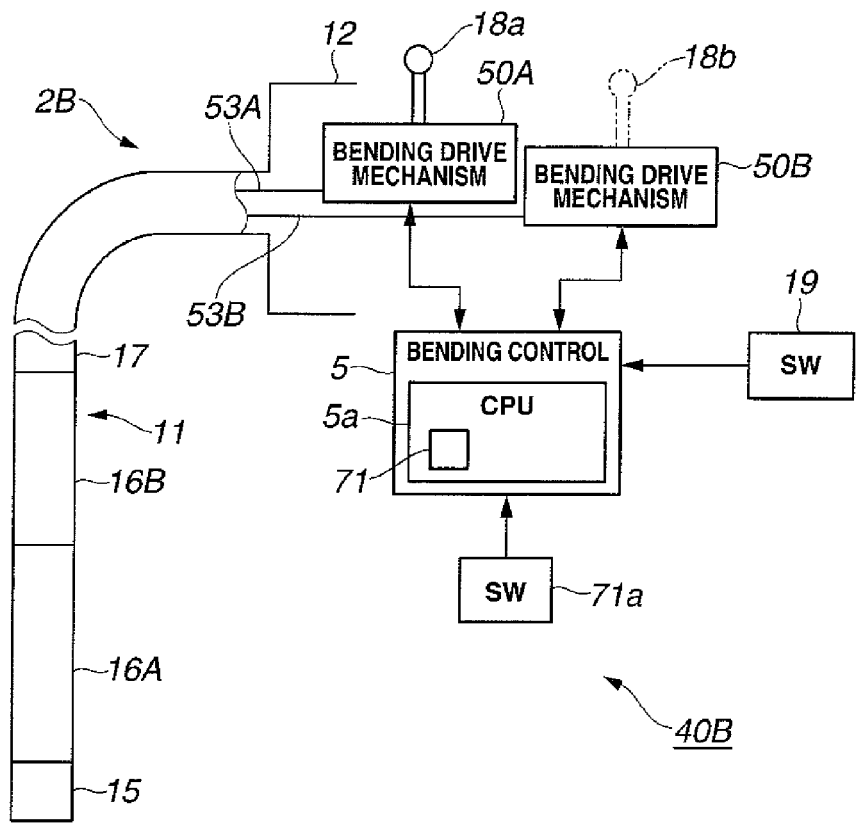
FIG. 9 illustrates a configuration of a bending control apparatus in a second embodiment of the present invention.

FIG. 9 illustrates a configuration of a part around a bending control apparatus 40B according to the second embodiment.

The first bending portion 16A and the second bending portion 16B are connected to a first bending drive mechanism 50A and a second bending drive mechanism 50B via angle wires 53A (53A represents 53u, 53d, 53l and 53r in FIG. 2) and 53B (53B also has a configuration similar to that of 53A) for driving bending of the first bending portion 16A and the second bending portion 16B, respectively.

The first bending drive mechanism 50A and the second bending drive mechanism 50B are connected to a bending control section 5 included in a CPU 5a, and the CPU 5a controls the operation of the first bending drive mechanism 50A and the second bending drive mechanism 50B.

The first bending drive mechanism 50A and the second bending drive mechanism 50B are provided with joysticks 18a and 18b, respectively. In the present embodiment, the joystick 18b is not essential.

Also, an insertion mode selection switch 19 is connected to the bending control section 5.

Upward/downward and leftward/rightward bending directions for the first bending portion 16A and upward/downward and leftward/rightward bending directions for the second bending portion 16B are arranged so as to be somewhat shifted from each other in order to avoid interference between the angle wires 53A and 53B for the both, which are inserted through the insertion portion 11.

Furthermore, due to an external force resulting from contact with the wall surface of an intestinal tract, the first bending portion 16A and the second bending portion 16B are passively bent (curved), and thus, a bending drive direction detected from rotational angles of pulleys corresponding to a bending angle of the first bending portion 16A and rotational angles of pulleys corresponding to a bending angle of the second bending portion 16B, and an actual bending drive direction may be shifted from each other.

In the present embodiment, a function that controls bending driving for the second bending portion 16B so as to follow a state of control of bending driving for the first bending portion 16A is provided.

In other words, in the present embodiment, a function that performs bending driving control for determining a bending drive direction for the second bending portion 16B from a bending drive direction of the first bending portion 16A is provided.

Accordingly, for example, the CPU 5a has a function of a setting section 71, which sets a bending drive range for the first bending portion 16A in a possible bending drive range of the first bending portion 16A as a first bending drive range.

As a result of a surgeon operating a setting switch 71a of the setting section 71, the setting section 71 sets the first bending drive range to an instructed value.

Then, when the first bending portion 16A has reached a limit of the first bending drive range (abbreviated as "bending limit"), the bending control section 5 performs control so as to drive bending of the second bending portion 16B.

Figure 10:
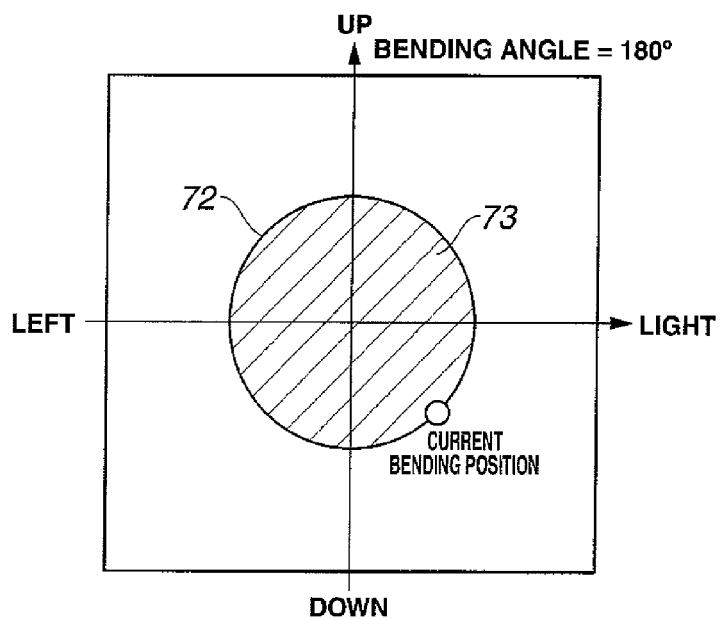
FIG. 10 is a diagram illustrating a case where bending of a second bending portion is driven.

FIG. 10 illustrates a bending limit 72 set as the possible bending drive range for the first bending portion 16A, and a state in which a current bending position of the first bending portion 16A has reached the bending limit 72. The region indicated by shaded lines within the bending limit 72 is a first bending drive range 73 set by the setting section 71.

For a bending drive direction for the bending control section 5 to drive bending of the second bending portion 16B in the present embodiment, as in the first embodiment, the second bending portion 16B is moved parallel to a plane formed by the first bending portion 16A or in a direction that is the same as the bending drive direction of the first bending portion 16A (in this case, a slight shift occurs as described above).

The rest of the configuration is substantially similar to that of the first embodiment. A bending start switch 74 indicated by a dotted line in FIG. 9 is used in a third embodiment.

Figure 11:
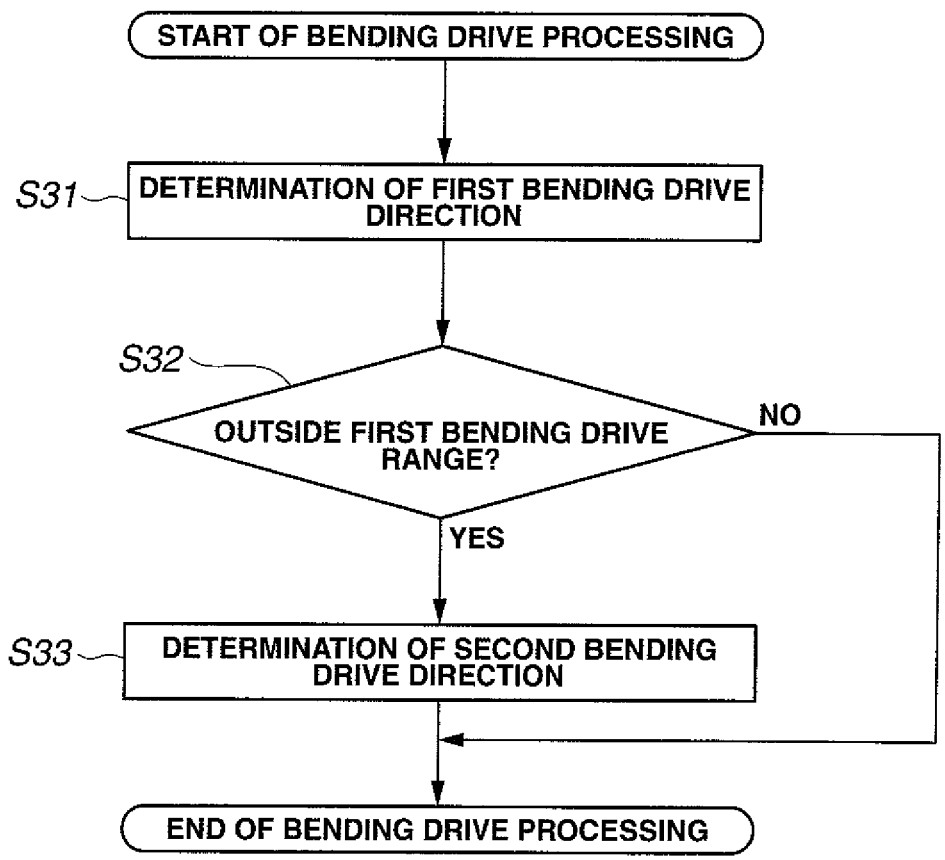
FIG. 11 is a flowchart illustrating a procedure of bending drive processing in the second embodiment.

FIG. 11 illustrates a procedure for bending drive processing in an automatic bending mode in the present embodiment. When bending drive processing is started, in the first step S31, the CPU 5a determines a bending drive direction for the first bending portion 16A as a first bending drive direction as in the first embodiment.

Then, the CPU 5a controls the first bending drive mechanism 50A, and the first bending drive mechanism 50A drives bending of the first bending portion 16A in the first bending drive direction.

In the next step S32, the CPU 5a monitors a bending drive range in which the bending of the first bending portion 16A has been driven, and determines whether or not the bending drive range falls outside the first bending drive range 73, that is, falls beyond the bending limit 72.

If the case falls under an affirmative result of the determination, in the next step S33, the CPU 5a keeps the first bending portion 16A at the bending limit 72, and determines the bending drive direction for the second bending portion 16B as a second bending drive direction.

Then, the CPU 5a controls the second bending drive mechanism 50B, and the second bending drive mechanism 50B drives bending of the second bending portion 16B in the second bending drive direction. Then, the processing in FIG. 11 is terminated. Also, if the case does not fall under an affirmative result of the determination in step S32, the processing in FIG. 11 is also terminated.

Figure 12:
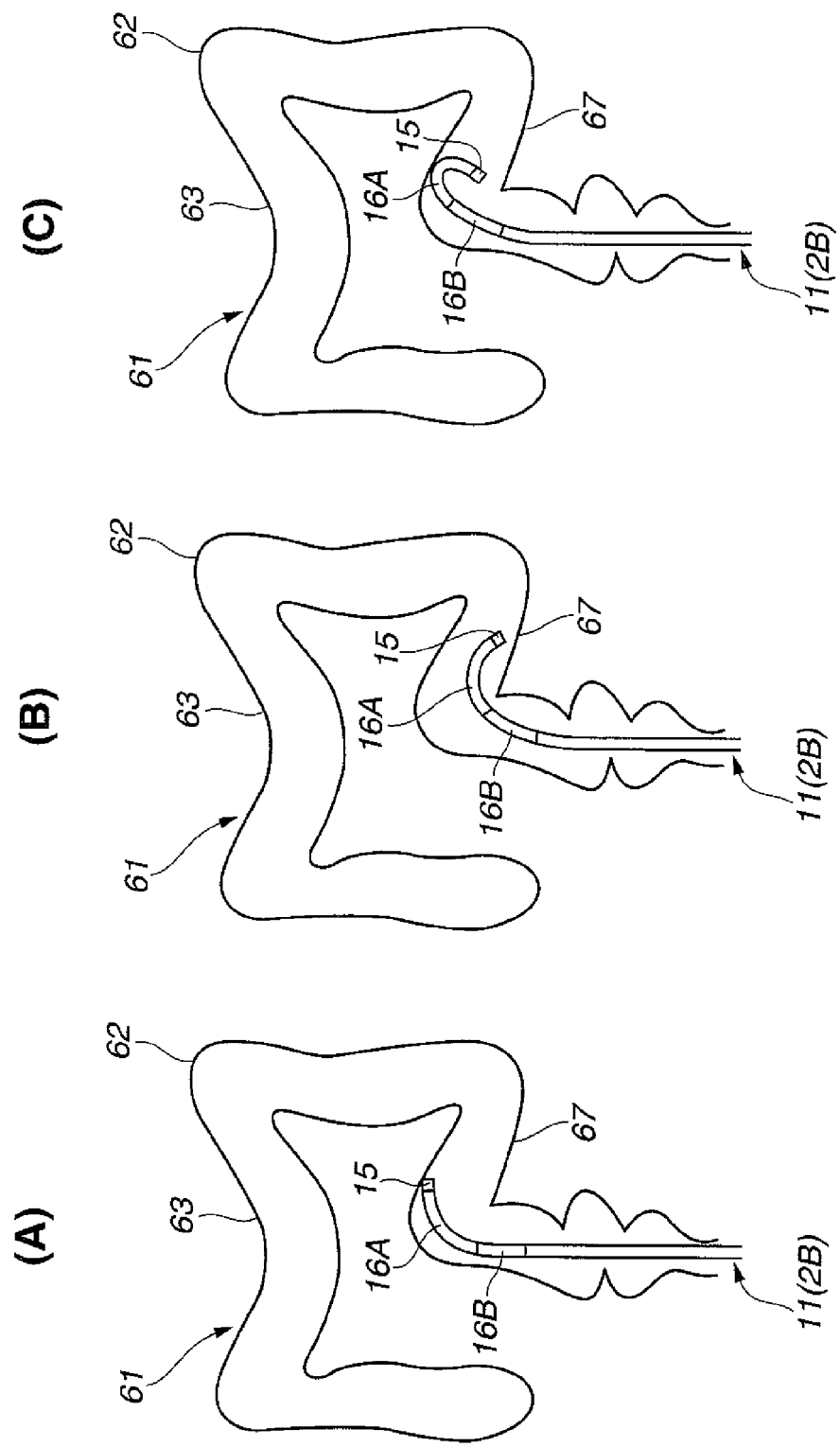
FIG. 12 is a diagram illustrating a case where a distal end side of an insertion portion is inserted into a large intestine in the second embodiment.

FIG. 12 illustrates a diagram illustrating an operation for a case where the insertion portion 11 of the endoscope 2B according to the present embodiment is inserted into a large intestine 61. An operation for insertion from a splenic flexure 62 to a transverse colon 63 side is substantially similar to that in the first embodiment, and thus, a description will be provided for a case of a site different from the part around the splenic flexure 62 in the first embodiment.

FIG. 12(A) indicates a state in which the first bending portion 16A is inserted from a region around a rectum to a sigmoid colon 67 side, and indicates a state in which the first bending portion 16A has reached the bending limit 72 of the first bending drive range 73 as a result of bending of the first bending portion 16A being driven in the first bending drive direction.

Then, if the CPU 5a determines a first bending drive direction beyond the bending limit 72, the CPU 5a drives bending of the second bending portion 16B, with the first bending portion 16A kept in the bending drive state at the bending limit 72.

In this case, the distal end side of the insertion portion 11 is in a state as illustrated in FIG. 12(B), facilitating smooth insertion. Failure of restriction of the bending drive range of the first bending portion 16A as in the present embodiment may result in difficulty in smooth insertion because the bending angle of the first bending portion 16A has an excessively sharp curve (with a small curvature radius) as illustrated in FIG. 12(C). The present embodiment can eliminate such difficulty.

The other operations and/or effects are similar to those of the first embodiment. As described above, the present embodiment can eliminate difficulty in insertion caused as a result of the first bending portion 16A being excessively bent, in addition to the effects of the first embodiment.

Third Embodiment

Figure 13:
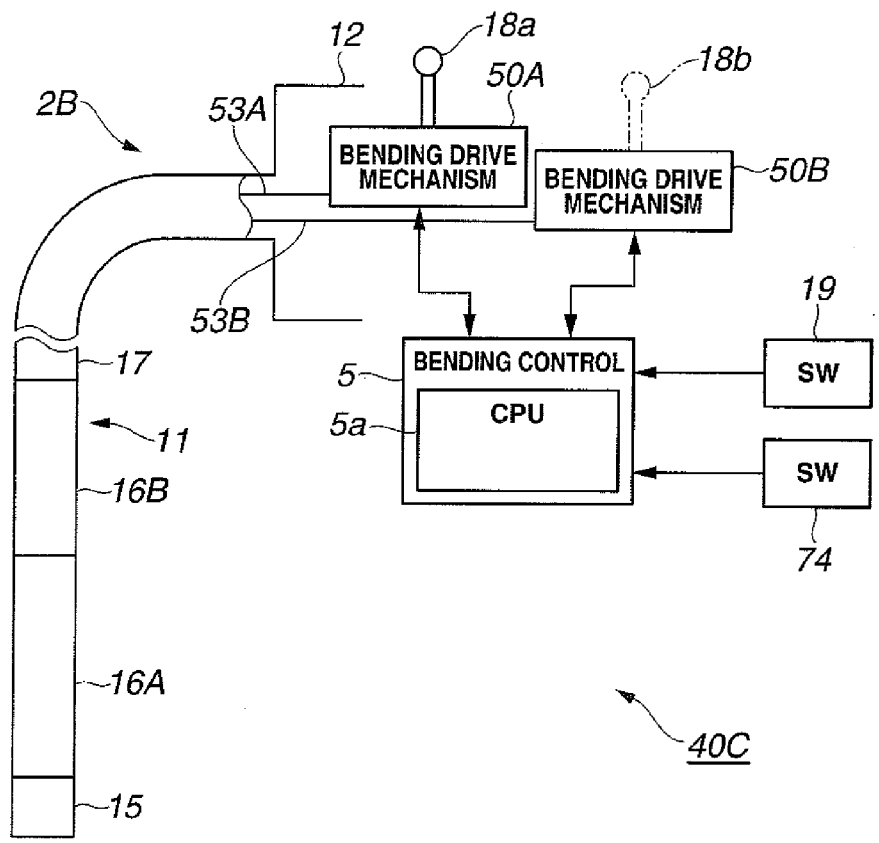
FIG. 13 illustrates a configuration of a bending control apparatus in a third embodiment of the present invention.

Next, the third embodiment of the present invention will be described. FIG. 13 illustrates a configuration of a bending control apparatus 40C according to the present embodiment. The bending control apparatus 40C is further provided with a bending start switch 74 in the bending control apparatus 40B illustrated in FIG. 9 in the second embodiment. The setting section 71 and the setting switch 71a have been removed.

In the second embodiment, the bending control section 5 performs control so as to drive bending of the second bending portion 16B with the first bending portion 16A kept at the bending limit 72 when the first bending portion 16A falls beyond the bending limit 72.

In the present embodiment, only during the period in which the bending start switch 74 is on, a bending control section 5 performs control to drive bending of a second bending portion 16B in a first bending drive direction for a first bending portion 16A.

Instead of the bending start switch 74, a configuration in which the amount of driving bending of the second bending portion 16B is adjusted according to an operation of, e.g., a lever enabling an instruction to be inputted in an analog amount may be employed.

Figure 14:
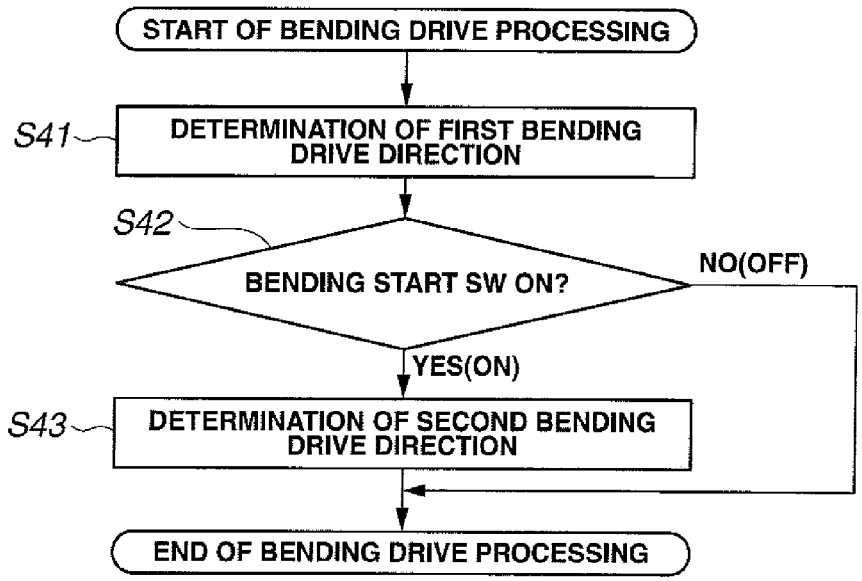
FIG. 14 is a flowchart illustrating a procedure of bending drive processing in the third embodiment.

Next, bending drive processing in an automatic bending mode in the present embodiment will be described with reference to FIG. 14.

When the bending drive processing is started, in the first step S41, a CPU 5a determines a bending drive direction for the first bending portion 16A as a first bending drive direction as in the first embodiment.

Then, the CPU 5a controls a first bending drive mechanism 50A, and the first bending drive mechanism 50A drives bending of the first bending portion 16A in the first bending drive direction.

In the next step S42, the CPU 5a determines whether or not the bending start switch is turned on. If the bending start switch is turned on, in the next step S43, the CPU 5a keeps the first bending portion 16A in its bending drive state immediately before the turning-on of the bending start switch, and determines the bending drive direction for the first bending portion 16A from then on as a second bending drive direction for the second bending portion 16B.

Then, the CPU 5a controls a second bending drive mechanism 50B, and the second bending drive mechanism 50B drives bending of the second bending portion 16B in the second bending drive direction. Then, the processing in FIG. 13 is terminated. Also, if the case does not fall under an affirmative result of the determination in step S42, the processing in FIG. 13 is also terminated.

The present embodiment provides effects similar to those of the second embodiment. In the present embodiment, when a surgeon drives bending of the first bending portion 16A, if the curvature radius of the bending is too small only with the first bending portion 16A, the bending start switch is turned on, enabling bending driving without the curvature radius being overly small. The present embodiment provides other effects similar to those of the first embodiment.

As a first variation of the present embodiment, a configuration including the function of the second embodiment and the function of the third embodiment may be provided. For example, in the configuration in FIG. 13, while the setting section 71 and the setting switch 71a are provided, a selection switch for selection (switch) between the function of the second embodiment and the function of the third embodiment may be provided.

In this case, the operations and/or effects of the second embodiment and the third embodiment are provided.

Furthermore, as a second variation, when the bending start switch 74 is turned on, the bending drive state may be made to transit from a bending drive state of the first bending portion 16A to a bending drive state of the second bending portion 16B with a distal end portion direction of the distal end portion 15 maintained.

In such case, the CPU 5a in the bending control section 5 controls the second bending portion 16B to be bent (within a largest possible bending angle range), while moving the first bending portion 16A back to a neutral position (a position with no bending), in order to maintain the distal end portion direction of the distal end portion 15.

Figure 15:
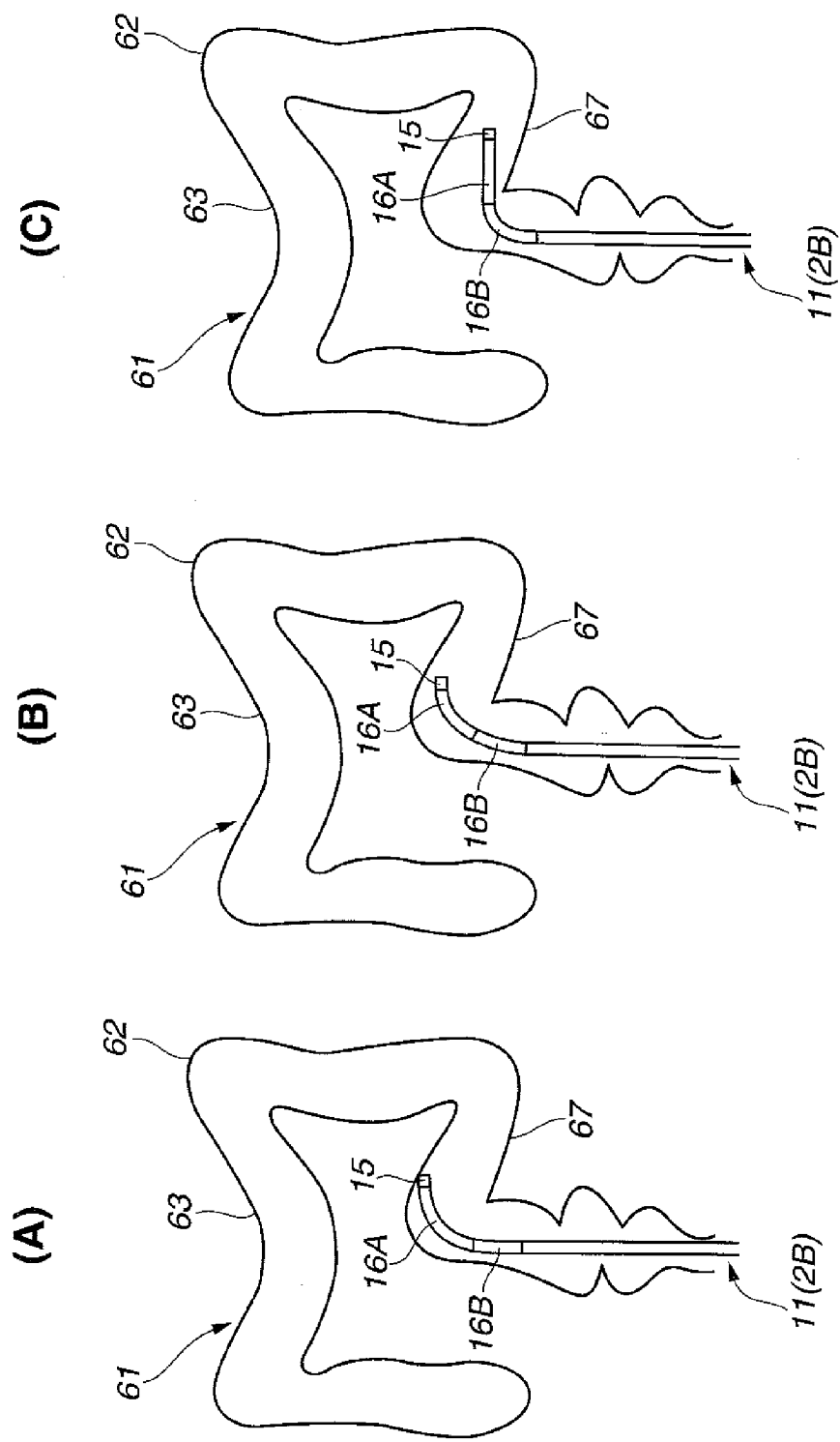
FIG. 15 is a diagram illustrating a case where a distal end side of an insertion portion is inserted into a large intestine in the third embodiment.

FIG. 15 is a diagram illustrating an operation of the second variation. FIG. 15(A) illustrates a bending state when the bending start switch 74 is turned on. In this state, only bending of the first bending portion 16A is driven. In FIG. 15(A), the distal end portion direction of the distal end portion 15 is, for example, a rightward direction.

The CPU 5a in the bending control section 5 provides the bending state illustrated in FIG. 15(C) through the intermediate step illustrated in FIG. 15(B), and then, terminates the operation of the second variation. The present variation enables the bending states of the bending portions 16A and 16B to be changed with the distal end portion direction of the distal end portion 15 maintained.

Fourth Embodiment

Figure 16:
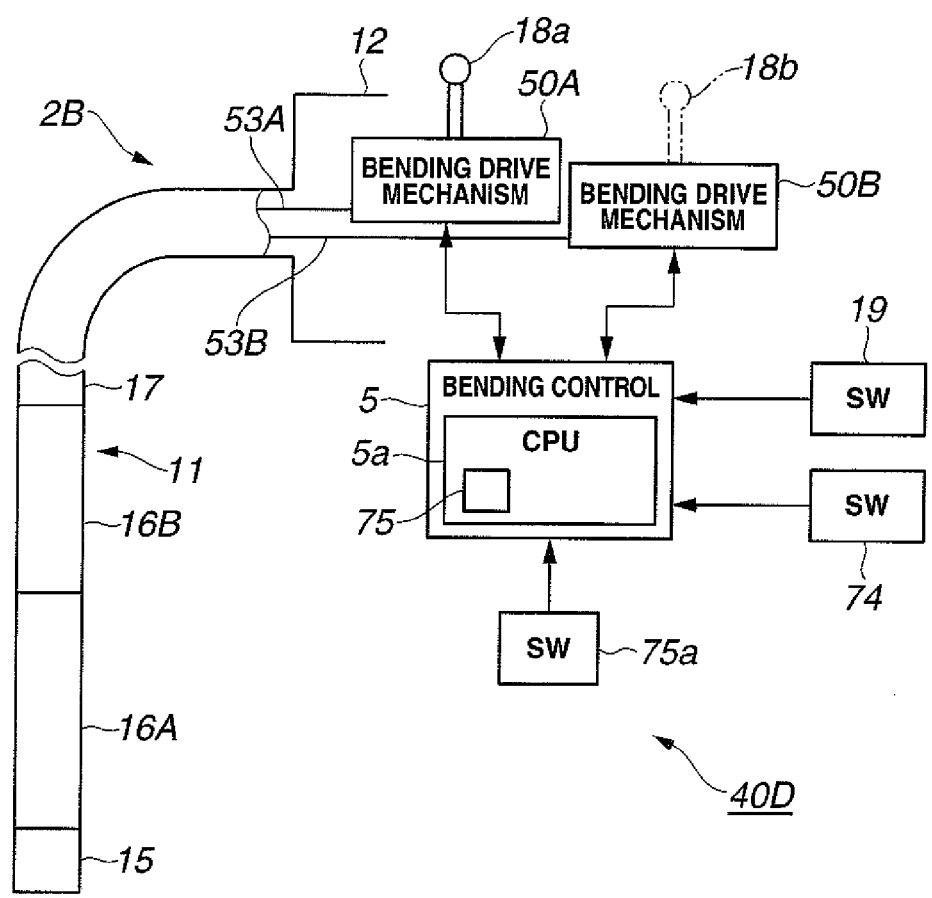
FIG. 16 illustrates a configuration of a bending control apparatus in a fourth embodiment of the present invention.

Next, a fourth embodiment of the present invention will be described. FIG. 16 illustrates a configuration of a bending control apparatus 40D in the present embodiment.

The bending control apparatus 40D further includes an adjustment section 75 that adjusts (sets) a drive ratio for simultaneously driving bending of a first bending portion 16A and a second bending portion 16B in the configuration in FIG. 13. The adjustment section 75 is provided by a processing function of a CPU 5a. Also, selection of the drive ratio can be made by means of a selection operation via a switch 75a.

In the present embodiment, when the bending start switch 74 is off, an operation similar to that of the third embodiment is performed. On the other hand, when the bending start switch 74 is on, the adjustment section 75 provided by the CPU 5a simultaneously drives bending of the first bending portion 16A and the second bending portion 16B at the drive ratio selected via the switch 75a.

The drive ratio selected via the switch 75a is set to a drive ratio of 1 as a default value.

A surgeon can adjust an instructed value for the drive ratio for driving bending of the first bending portion 16A and the second bending portion 16B, via the adjustment section 75.

FIG. 17 is a diagram illustrating contents of control performed by the CPU 5a in a bending control section 5 in the present embodiment.

FIG. 17 illustrates a current first bending position W1 and a current second bending position W2 for the first bending portion 16A and the second bending portion 16B. When the bending start switch 74 is turned on in such state, the CPU 5a determines a target first bending position Wt1 and a target second bending position Wt2 with, for example, a center position on a line connecting the current first bending position W1 and the current second bending position W2 set as the target bending positions. Here, the description has been provided in terms of the case where the drive ratio is set to 1.

Then, the CPU 5a performs control to drive bending of the first bending portion 16A and the second bending portion 16B so as to reach the target first bending position Wt1 and the target second bending position Wt2, respectively. It should be noted that change of the drive ratio via the switch 75a enables change of the positions of the target first bending position Wt1 and the target second bending position Wt2.

Where a description is provided in terms of bent shapes of the first bending portion 16A and the second bending portion 16B, the shapes illustrated in FIGS. 18(A) and 18(B) are provided.

For example, as illustrated in FIG. 18(A), when bending of only the first bending portion 16A is driven, the bending of the first bending portion 16A may be driven excessively. In such state, it is difficult to insert the first bending portion 16A into a deep part side of a sigmoid colon 67.

In such case, by means of turning the bending start switch 74 on, bending of the first bending portion 16A and the second bending portion 16B can be driven so as to have a same curvature radius (curve radius) and a same target bending position as illustrated in FIG. 18(B).

When the settings are made to provide the state illustrated in FIG. 18(B), the insertion into a deep part side of a sigmoid colon 67 is facilitated.

As described above, according to the present embodiment, bending of the first bending portion 16A and bending of the second bending portion 16B are driven simultaneously, and the drive ratio for the case can variably be set, enabling provision of bending driving suitable for an insertion site compared to the case where bending of only the first bending portion 16A is driven in Japanese Patent Application Laid-Open Publication No. 2006-116289.

Furthermore, embodiments provided by, e.g., partially combining the above-described embodiments also belong to the present invention.

What is claimed is:

1. An endoscope apparatus comprising:
    an insertion portion including a bendable bending portion provided on a distal end side thereof;
    a bending drive section that drives bending of the bending portion;
    an insertion shape detection section that detects an insertion shape of the insertion portion as insertion shape information;
    a curved position calculation section that calculates a curved position at which the insertion portion inserted in a curved tubular body cavity is curved in a curved region of the tubular body cavity, as curved position information, based on the insertion shape information;
    a curved state calculation section that calculates a curved attitude of the insertion portion, with the curved position as reference, as curved state information, based on the curved position information and the insertion shape information;
    a bending drive plane calculation section that calculates a bending drive plane on which the bending portion is driven such that the curved region of the tubular body cavity is brought into a straightened state, as bending drive plane information, based on the curved state information;
    a curve direction calculation section that calculates a curve direction of the insertion portion on the bending drive plane, as curve direction information, based on the curved state information and the bending drive plane information; and
    a control section that outputs to the bending drive section a control signal for driving the bending portion on the bending drive plane, with a direction opposite to the curve direction as a bending drive direction, based on the curved state information.

2. The endoscope apparatus according to claim 1, wherein the control section performs control to drive bending of the bending portion parallel to the bending drive plane, using information on the bending drive plane.

3. The endoscope apparatus according to claim 2, further comprising an azimuth detection section that detects a predetermined bending direction in the bending portion as a reference azimuth,
    wherein, based on an angle formed by the bending drive plane with the reference azimuth which is calculated based on information on the estimated bending drive plane and information on the reference azimuth, the control section performs control to drive bending of the bending portion parallel to the bending drive plane in a direction which forms the angle from the reference azimuth.

4. The endoscope apparatus according to claim 3, wherein the control section conducts a principal component analysis for a plurality of coordinates obtained along a longitudinal direction of the insertion portion on the distal end side of the insertion portion in which the bending drive plane is included to estimate the bending drive plane.

5. The endoscope apparatus according to claim 4, wherein the control section performs control to drive bending of the bending portion in a direction opposite to a curve direction on the bending drive plane in which the distal end side of the insertion portion is curved.

6. The endoscope apparatus according to claim 2, further comprising an azimuth detection section that detects a predetermined bending direction in the bending portion as a reference azimuth,
    wherein the control section further sets a virtual plane in the vicinity of a distal end of the insertion portion, with an axis direction of the insertion portion as a normal direction thereof, calculates an intersection line between the virtual plane and the bending drive plane, and calculates an angle formed by the intersection line with the reference azimuth.

7. The endoscope apparatus according to claim 6, wherein the control section determines a direction of the angle to be a bending drive direction to drive bending of the bending portion from a current bending position of the bending portion, and performs control to drive bending of the bending portion in the direction of the angle.

8. The endoscope apparatus according to claim 7, wherein the control section performs control to drive bending of the bending portion in a direction opposite to a curve direction on the bending drive plane in which the distal end side of the insertion portion is curved.

9. The endoscope apparatus according to claim 2, wherein the control section conducts a principal component analysis for a plurality of coordinates obtained along a longitudinal direction of the insertion portion on the distal end side of the insertion portion in which the plane is included to estimate the bending drive plane.

10. The endoscope apparatus according to claim 1, wherein the control section conducts a principal component analysis for a plurality of coordinates obtained along a longitudinal direction of the insertion portion on the distal end side of the insertion portion in which the plane is included to estimate the bending drive plane.

11. The endoscope apparatus according to claim 10, wherein a second bending portion is provided at a proximal end of the bending portion on the distal end side of the insertion portion.

12. The endoscope apparatus according to claim 11, wherein the control section performs control to drive bending of the second bending portion so as to follow a state of control to drive bending of the bending portion.

13. A bending drive control method comprising a computer programmed to perform:

a curve plane estimation step of estimating a curve plane including a distal end side of an insertion portion, the insertion portion including a bendable bending portion provided thereon, when the distal end side of the insertion portion is inserted along a curved curve shape in a tubular body cavity;

a virtual plane setting step of setting a virtual plane in the vicinity of a distal end of the insertion portion, with an axis direction of the distal end side of the insertion portion as a normal direction thereof; and a bending drive direction determination step of determining a bending drive direction to drive bending of the bending portion, based on an angle formed by an intersection line between the curve plane and the virtual plane with a predetermined bending direction in the bending portion.

14. The bending drive control method according to claim 13, wherein the curve plane estimation step includes estimating the curve plane from a result of estimation in which three mutually-orthogonal principal component directions are estimated using a principal component analysis of a plurality of coordinate positions on the distal end side of the insertion portion inserted along the curve shape.

* * * * *